United States Patent
Ahrens et al.

(10) Patent No.: US 6,822,132 B2
(45) Date of Patent: Nov. 23, 2004

(54) DRESSING

(75) Inventors: Helge Ahrens, Hamburg (DE); Carsten Hartkopf, Hamburg (DE); Jochen Kenndoff, Jawa Timur (ID); Ulrich Köhler, Hamburg (DE); Dirk Lenz, Cranfield (GB); Robert Mayan, Buxtehude (DE); Günther Sachau, Quickborn (DE); Ingrid Wesselkamp, Hamburg (DE)

(73) Assignee: Beiersdorf AG, Hamburg (DE)

( * ) Notice: Subject to any disclaimer, the term of this patent is extended or adjusted under 35 U.S.C. 154(b) by 137 days.

(21) Appl. No.: 09/951,089

(22) Filed: Sep. 13, 2001

(65) Prior Publication Data

US 2002/0156411 A1 Oct. 24, 2002

(30) Foreign Application Priority Data

Sep. 22, 2000 (DE) .......................................... 100 47 673

(51) Int. Cl.$^7$ ................................................. A61F 5/00
(52) U.S. Cl. .......................................... 602/41; 602/43
(58) Field of Search ............................. 602/41–59, 336; 424/444–449

(56) References Cited

U.S. PATENT DOCUMENTS

| | | | | | |
|---|---|---|---|---|---|
| 4,377,159 | A | * | 3/1983 | Hansen | 602/53 |
| 5,512,041 | A | * | 4/1996 | Bogart | 602/58 |
| 5,591,447 | A | * | 1/1997 | Jensen | 424/443 |
| 5,844,013 | A | * | 12/1998 | Kenndoff et al. | 521/137 |
| 6,264,976 | B1 | * | 7/2001 | Heinecke et al. | 424/443 |
| 2002/0160037 | A1 | * | 10/2002 | Ahrens et al. | 424/445 |

* cited by examiner

Primary Examiner—John J. Calvert
Assistant Examiner—Linh Truong
(74) Attorney, Agent, or Firm—Norris McLaughlin & Marcus

(57) ABSTRACT

A dressing especially for covering wounds or preventing or treating blisters, comprising a water vapor pervious carrier film uniformly covered with an adhesive layer, wherein there is centrally disposed on the adhesive layer a water vapor pervious polyurethane matrix which is beveled from an especially central point to the edge of the adhesive layer, although the periphery of the adhesive layer is at least partially not covered by the polyurethane matrix.

9 Claims, 2 Drawing Sheets

DRESSING

Figure 1:
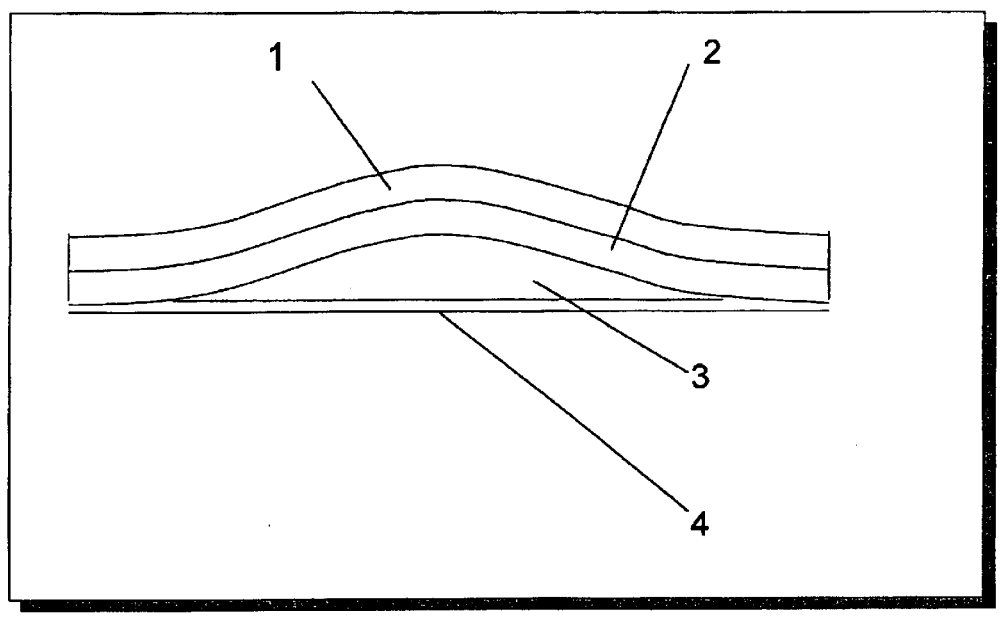

This invention relates to a multi-ply dressing which can be used especially at pressure points, on blisters and open blisters on the heel, on the ball of the thumb and on the fingers.

Pressure points, blisters and open blisters on the heel, on the ball of the thumb and on the fingers are customarily cared for with conventional plaster products consisting of a textile carrier material, a pressure sensitive adhesive layer and a nonwoven wound contact material.

Proven products of this type are available for example from Beiersdorf, for example under the name of Hansaplast® elastic or Hansaplast® classic.

Plasters of this type, however, have some disadvantages in use:

Friction in the shoe causes gradual detachment of the plaster
Soiling of the carrier material on prolonged wearing
Little cushioning
Pressure points at the edge of the plaster
Painful removal Modern wound management products such as hydrocolloids (see for example "Hydrokolloide" by R. Lipmann in "Medical Device & Diagnostic Industry", June 1999), which were developed for colostomy and professional wound management applications, are increasingly used for pressure points and blisters.

Wound management products based on hydrocolloids have advantages over traditional plasters. They generate a moist wound healing medium which stops the wound drying out and creates an optimal medium for rapid wound healing. Further advantages are the inconspicuity in use, secure adherence, absorption of exudate (from a blister for example), good cushioning and painless removability.

Typical compositions of the first commercially available hydrocolloids for wound management products comprise:

Low molecular weight polyisobutylene (40% by weight),
Pectin (20% by weight),
Sodium carboxymethylcellulose=CMC (20% by weight)
Gelatin (20% by weight)

Modern hydrocolloid formulations, known as integrated formulations, as available for example from Coloplast, are based on styrene-isoprene-styrene block polymers with hydrocarbon resins as tackifiers, mineral oil as a plasticizer and also CMC as an absorbent.

These formulations with SIS as scaffold formers contain glassy domains (styrene blocks) and thermoplastic domains (isoprene blocks). At room temperature, the glassy domains provide a kind of three-dimensional crosslinking structure, which disappears at higher temperature.

Hydrocolloids possess good wet tack even under moist conditions, so that they are very useful as blister plasters on the heel and palm of the hand, an application site involving a relatively high moisture loss from the skin.

EP 0 264 299 B1 discloses a dressing consisting of a water absorbent sealing pad which in turn is formed of one or more hydrocolloids. The hydrocolloid or hydrocolloids are dissolved in or mixed with a binder.

The pad is firmly and completely enclosed by a watertight cover layer. According to the invention, the pad is beveled at least along the outer periphery such that the thickness at the edge does not exceed about one quarter of its maximum thickness.

Hydrogels are macromolecular, natural or synthetic materials which contain a high level of hydrophilic groups and are consequently capable of absorptively binding water. The water absorption capacity of many hydrogels is the multiple of their own weight in the water-free state.

Hydrogels are used in wound management in various forms, since they protect wounds against drying out, absorb wound exudate, serve as a matrix for active substances of all kinds and also as a basis for colonization with autologous or heterologous skin cells.

Hydrogels may be used in the form of foams, inter alia. Foams for managing skin wounds or surgical wounds are known per se to one skilled in the art. Polyurethane foams or collagen foams are used in the main.

Self-adhesive gel foams are likewise known to one skilled in the art. They are generally readily fixable on the skin, but usually have the disadvantage that their water absorption capacity and their water retention capacity are substantially limited.

Also known are hydrophilic foams of polyurethane gels. WO 88/01878 A1 describes self-adhesive polyurethane foams or polyurethane foam gels which can contain copolymerized methacrylate units among others. These foam gels are produced by adding water.

Polyurethane gels based on a polyurethane matrix and high molecular weight polyols are also described in EP 0 057 839 B1. Self-adhesive sheet materials comprising polyurethane gels are known from EP 0 147 588 B1. The polyurethane gels disclosed in these last two references cited are unfoamed.

The self-adhesive gels have isocyanate indexes of 15 to 70 (EP 0 147 588 A2).

EP 0 196 364 A2 describes hydrophilic polyurethane foams which may be filled with water absorbent polymers based on a copolymer of acrylic acid and potassium acrylate and are intended for medical purposes. The polyurethane is prepared on the basis of MDI. The polyether used has a minimum functionality of two hydroxyl groups, preferably two to three hydroxyl groups in each case. The NCO/OH ratio is stoichiometric. The polyurethane is accordingly not gellike. It can be foamed with pressurized air or with other gases which do not react with isocyanate or by means of low-boiling solvents. Absorbent and polyetherpolyol are mixed in a ratio of about 3:1. The foam has adhesive properties on wounds, which have to be completely eliminated by means of an aluminized veil in order that the foam may be used for wound treatment.

Foam wound contact materials as obtainable for example from Beiersdorf under the name of Cutinova® thin and Cutinova® hydro are described inter alia in DE 42 33 289 A1, in DE 196 18 825 A1 and WO 97/43328.

According to these references, the polyurethane gel foam consists of a polyaddition product of a polyetherpolyol (Levagel® from Bayer AG) with an aromatic or aliphatic diisocyanate (Desmodur® Bayer AG), into which a polyacrylate superabsorbent powder (Favor®, Stockhausen) has been incorporated. The polyurethane gel can be made weakly or strongly self-adherent to skin depending on the ratio of OH equivalents of the polyol to reactive isocyanate groups.

The sheetlike polyurethane gel foam from 1 to 6 mm in thickness is covered by a polyurethane foam on one side. Plasters of appropriate size are punched out of the bale material. The wound contact material thus produced surprisingly abheres completely on absorption of wound fluid and, in the process, does not show the tendency, known from hydrocolloids, to disintegrate on pronounced swelling, which may lead to residues of the hydrocolloid to remain in the wound.

The punched-out large-area wound contact materials are very useful for managing chronic or slow-healing wounds of patients who have to be treated in hospital.

In the case of smaller minor injuries or blistering due to pressure points on the hand, ball and heel, however, this product construction has some disadvantages.

The product tends to curl under mechanical loading, owing to its punching edges. The open punching edges prove to be a disadvantage on contact with moisture, since they provide a way for water to get into the absorbent layer and cause swelling and abhering of the polyurethane gel.

Finally, blister management additionally utilizes traditional plasters (for example the Hansaplast® classic fabric plaster from Beiersdorf) which are only contingently useful as blister plasters for the care of pressure points or damaged horny skin on highly contoured parts of the body.

Disadvantages prove to be the low elasticity and the tendency for the carrier material to curl up at the edges of the plaster when subjected to mechanical loading in the course of prolonged wear. Additionally, the plaster is substantially wetted through in the course of daily ablutions or hand washing and loses adhesion.

Traditional plasters are visually very conspicuous, hinder movements and impair the wear comfort in shoes.

It is an object of the present invention to provide a dressing which is capable of absorbing exudate from pressure points, which is well cushioned, which has a sufficient transmission rate for moisture from the horny skin through the plaster to the outside and which creates a moist wound healing medium.

Accordingly, the invention provides a dressing especially for covering wounds or preventing or treating blisters, comprising
a water vapor pervious carrier film uniformly covered with
an adhesive layer, wherein
there is centrally disposed on the adhesive layer a water vapor pervious polyurethane matrix which is beveled from an especially central point to the edge of the adhesive layer, although the periphery of the adhesive layer is at least partially not covered by the polyurethane matrix.

More particularly, the point is situated at the area's midpoint in order that a symmetrical appearance may be obtained for the plaster. But the beveling may also be uneven, depending on the requirements and application scenario of the plaster.

This results in a very wide variety of shapes. The matrix may for example have a lenticular or semispherical shape.

The carrier film preferably comprises a transparent multilayered water vapor pervious polyurethane film which, in a further advantageous embodiment, is from 60 to 80 μm in thickness.

The advantageous thickness results from the need for a flexurally stiff material which resists curling when subjected to mechanical loading.

The upper layer, furthermore preferably comprises a hard polyurethane coating which creates a surface having a particularly low stick and slip friction, which has been determined to be advantageous for application in the realm of pressure points and/or blisters.

The adhesive layer, preferably from 35 to 50 μm in thickness, must be considered thin. In a further advantageous embodiment, it comprises a skin-friendly pressure adhesive composition comprising polyacrylate into which a tackifier (a hydrocarbon resin for example) is incorporated to enhance the adhesion to skin.

The water vapor pervious outer pressure adhesive layer does not store any moisture and so protects the central liquid-absorbing adhesive layer against the ingress of water from the outer edge (sealing) and, through a very thin execution in the edge region, prevents possible curling (in a shoe for example).

The polyurethane matrix is especially transparent, substantially water vapor pervious and adhesive. To store liquid, it is preferable to incorporate a polyacrylate-based superabsorbent polymer as a powder.

The polyurethane matrix serves as good cushioning (convex shape, maximum thickness preferably about 1.6 mm) and as a storage medium for exudate from the pressure point and/or blister.

Useful polyurethanes form part of the subject matter of DE 196 18 825, which discloses hydrophilic, self-adhesive polyurethane gels consisting of
a) polyetherpolyols with 2 to 6 hydroxyl groups and having OH values of 20 to 112 and an ethylene oxide (EO) content of $\geq 10$ weight %,
b) antioxidants,
c) bismuth(III) carboxylates soluble in the polyols a) and based on carboxylic acids having 2 to 18 carbon atoms as catalysts and also
d) hexamethylene diisocyanate,
wherein the product of the functionalities of the polyurethane-forming components a) and d) is at least 5.2, the quantity of catalyst c) amounts to 0.005 to 0.25 weight %, relative to the polyol a), the quantity of antioxidants b) is in the range from 0.1 to 1.0 weight %, based on polyol a), and the ratio of free NCO groups of component d) to the free OH groups of component a) (isocyanate index) is selected within the range from 0.30 to 0.70.

Preference is given to using polyetherpolyols having 3 to 4, most preferably 4, hydroxyl groups and an OH number in the range from 20 to 112, preferably 30 to 56. The ethylene oxide content in the polyetherpolyols used according to the invention is preferably $\geq 20\%$ by weight.

Polyetherpolyols are known per se and are prepared for example by polymerization of epoxides, such as ethylene oxide, propylene oxide, butylene oxide or tetrahydrofuran, with themselves or by addition of these epoxides, preferably of ethylene oxide and propylene oxide—optionally mixed with each other or separately in succession—to starter components having at least two reactive hydrogen atoms, such as water, ethylene glycol, propylene glycol, diethylene glycol, dipropylene glycol, glycerol, trimethylolpropane, pentaerythritol, sorbitol or sucrose. Representatives of the useful high molecular weight polyhydroxy compounds mentioned are recited for example in High Polymers, Vol. XVI, "Polyurethanes, Chemistry and Technology" (Saunders-Frisch, Interscience Publishers, New York, volume 1, 1962, pages 32–42).

The isocyanate component used is monomeric or trimerized hexamethylene diisocyanate or hexamethylene diisocyanate modified by biuret, uretidione, allophanate groups or by prepolymerization with polyetherpolyols or mixtures of polyetherpolyols based on the known starter components with 2 or >2 reactive hydrogen atoms and epoxides, such as ethylene oxide or propylene oxide having an OH number of $\leq 850$, preferably 100 to 600. Preference is given to the use of modified hexamethylene diisocyanate, especially hexamethylene diisocyanate modified by prepolymerization with polyetherdiols of OH number 200 to 600. Very particular preference is given to modifications of hexamethylene diisocyanate with polyetherdiols of OH number 200–600 whose residual level of monomeric hexamethylene diisocyanate is below 0.5% by weight.

Useful catalysts for the polyurethane gels of the invention are bismuth(ill) carboxylates which are soluble in the water-free polyetherpolyols a) and are based on linear, branched, saturated or unsaturated carboxylic acids having 2 to 18, preferably 6 to 18, carbon atoms. Preference is given to Bi(III) salts of branched saturated carboxylic acids having tertiary carboxyl groups, such as 2,2-dimethyloctanoic acid (for example Versatic acids, Shell). Of particular suitability are formulations of these Bi(III) salts in excess fractions of these carboxylic acids. Of outstanding utility is a solution of 1 mol of the Bi(III) salt of versatic 10 acid (2,2-dimethyloctanoic acid) in an excess of 3 mol of this acid with a Bi content of about 17%.

The catalysts are preferably used in amounts from 0.03 to 0.1% by weight, based on polyol a).

Useful antioxidants for the polyurethane gels of the invention are in particular sterically hindered phenolic stabilizers, such as BHT (2,6-ditert-butyl-4-methylphenol), Vulkanox BKF (2,2'-methylenebis(6-tert-butyl-4-methylphenol) (Bayer AG), Irganox 1010 (pentaerythrityl tetrakis-[3-(3,5-ditert-butyl-4-hydroxyphenyl)propionate]), Irganox 1076 (octadecyl 3-(3,5-ditert-butyl-4-hydroxyphenyl)propionate) (Ciba-Geigy) or tocopherol (vitamin E). Preference is given to using those of the α-tocopherol type.

The antioxidants are preferably used in amounts from 0.15 to 0.5% by weight, based on polyol a).

The isocyanate index (ratio of the free NCO groups used in the reaction to the free OH groups) of the polyurethane gel compositions according to the invention is in the range from 0.30 to 0.70, preferably in the range from 0.45 to 0.60, depending on the functionality of the isocyanate and polyol components used. The isocyanate index required for gel formation is very simple to estimate by the following formula:

$$f_{(polyol)} \cdot (f_{(isocyanate)} - 1) \cdot index \approx 2$$

$$index \approx \frac{2}{f_{(polyol)} \cdot (f_{(isocyanate)} - 1)}$$

f: functionality of isocyanate or polyol component

Depending on the tackiness or elasticity required of the gel, the isocyanate index to be actually used may differ from the calculated value by up to +20%.

The polyurethane gel compositions of the invention are prepared by customary processes as described for example in Becker/Braun, Kunststoff-Handbuch, volume 7, Polyurethane, pages 121 ff, Carl-Hauser, 1983.

Preference is further given to the use of polyurethanes as disclosed in EP 0 665 856 B1.

The hydrophilic polyurethane gel foams are accordingly obtainable from 1. a polyurethane gel which comprises
    (A) 25–62% by weight, preferably 30–60% by weight, particularly preferably 40–57% by weight, based on the sum total of (A) and (B), of a covalently crosslinked polyurethane as a high molecular weight matrix and
    (B) 75–38% by weight, preferably 70–40% by weight, particularly preferably 60–43% by weight, based on the sum total of (A) and (B), of one or more polyhydroxy compounds which are firmly held in the matrix by secondary valence forces and have an average molecular weight between 1000 and 12,000, preferably between 1500 and 8000, particularly preferably between 2000 and 6000, and an average OH number between 20 and 112, preferably between 25 and 84, particularly preferably between 28 and 56, as a liquid dispersant, the dispersant being substantially free of hydroxy compounds having a molecular weight below 800, preferably belowe 1000, particularly preferably below 1500, and optionally
    (C) 0 to 100% by weight, based on the sum total of (A) and (B), of filler and/or additive substances,
and which is obtainable by reaction of a mixture of
    a) one or more polyisocyanates,
    b) one or more polyhydroxy compounds having an average molecular weight between 1000 and 12,000 and an average OH number of between 20 and 112,
    c) optionally catalysts or accelerants for the reaction between isocyanate groups and hydroxyl groups and also optionally
    d) filler and additive substances known per se from polyurethane chemistry,
wherein this mixture is substantially free of hydroxy compounds having a molecular weight below 800, the average functionality of the polyisocyanates ($F_I$) is between 2 and 4, the average functionality of the polyhydroxy compound ($F_p$) is between 3 and 6 and the isocyanate index (K) conforms to the formula $$K = \frac{300 \pm X}{(F_I \cdot F_p) - 1} + 7$$

where X is $\leq 120$, preferably X is $\leq 100$, particularly preferably X is $\leq 90$, and the K index has values between 15 and 70, the specified molecular weight and OH number averages being number averages, 2. a water absorbent material and
3. a nonaqueous foaming agent.

The polyurethane gels are preparable from the starting compounds known per se from polyurethane chemistry by processes known per se as described for example in DE 31 03 499 A1, DE 31 03 500 A1 and EP 0 147 588 A1. It is essential, however, that the above-defined conditions be adhered to for the selection of the gel-forming components, or nontacky, elastic gels will be obtained instead of self-adhesive gels.

Preferred polyhydroxy compounds are polyetherpolyols as more particularly specified in the above mentioned laid-open specifications.

Useful polyisocyanate components include not only (cyclo)aliphatic but also aromatic isocyanates. Preferred (cyclo)aliphatic polyisocyanates are 1,6-hexamethylene diisocyanate and also its biurets and trimers and hydrogenated diphenylmethane diisocyanate ("MDI") grades. Preferred aromatic polyisocyanates are those which are obtained by distillation, such as MDI mixtures of 4,4'- and 2,4'-isomers or 4,4'-MDI, and also toluylene diisocyanate ("TDI") grades.

The diisocyanates can be selected in particular for example from the group of the unmodified aromatic or aliphatic diisocyanates or else from modified products formed by prepolymerization with amines; polyols or polyetherpolyols.

The polyurethane gels may optionally contain additives known per se from polyurethane chemistry, for example fillers and short fibers based on inorganics or organics, metal pigments, surface-active substances or liquid extenders such as substances having a boiling point of above 150° C.

Useful organic fillers include for example baryte, chalk, gypsum, kieserite, sodium carbonate, titanium dioxide, cerium oxide, quartz sand, kaolin, carbon black and microballoons.

Useful organic fillers include for example powders based on polystyrene, polyvinyl chloride, urea-formaldehyde and polyhydrazodicarbonamide. Useful short fibers include for example glass fibers 0.1–1 mm in length or fibers of organic origin such as for example polyester or polyamide fibers. Metal powders, for example iron or copper powder, can likewise also be used in gel formation. To confer the desired color on the gels, it is possible to use the organic or inorganic dyes or color pigments known per se for the coloration of polyurethanes, for example iron oxide or chromium oxide pigments, phthalocyanine- or monoazo-based pigments. Useful surface-active substances include for example cellulose powder, active carbon and silica products.

To modify the adhesive properties of the gels, they may optionally include adds of polymeric vinyl compounds, polyacrylates and other copolymers customary in adhesive technology or else adhesives based on natural materials up to a level of 10% by weight, based on the weight of the gel composition.

Preferred water-absorbing materials are the water-absorbing salts, known as superabsorbents, of polyacrylates and copolymers thereof, especially the sodium or potassium salts, They may be crosslinked or uncrosslinked and are also obtainable as commercial products. Particularly suitable products are those disclosed in DE 37 13 601 A1 and also new-generation superabsorbents with only low remaining contents of water which can be dried out and high swelling capacity under pressure. Preferred products are lightly crosslinked polymers based on acrylic acid/sodium acrylate. Such sodium polyacrylates are obtainable as Favor 22-SK (Chemische Fabrik Stockhausen GmbH, Germany).

Further absorbents are likewise suitable, for example carboxymethylcellulose and karaya.

The degree of foaming can be varied within wide limits through the incorporated amounts of foaming agent.

Optionally, the self-adhesive product is covered up by siliconized paper or a, particularly siliconized, film, so that the adhesive side is protected during storage.

The transparent dressing of the invention exhibits prolonged adherence to highly contoured horny-skin areas of the human body, which is achieved through the specific product construction. The dressing exhibits good cushioning without impairing the wear comfort in the shoe through a specific convex plaster shape. Curling in the shoe of the plaster due to mechanical stress is prevented by a sufficiently thick and flexurally stiff carrier material.

An absorption of exudate from pressure points is provided by an adhesive polyurethane matrix containing superabsorbent.

Adequate moisture transport from the horny skin through the plaster to the outside is provided by a combination of suitable components of carrier and adhesive materials together with a simultaneous generation of a moist wound healing medium.

The novel dressing is notable for significantly prolonged wear time, very good comfort properties, residueless removability and visible inconspicuity compared with conventional plasters, i.e., exhibits optimal adhesion to horny skin areas (heel or ball of thumb) due to the central, substantially cushioning, liquid absorbent, weakly adhesive pressure adhesive zone and the strongly adhesive, nonabsorbent outer zone and of the particularly constructed water vapor pervious carrier material.

In what follows, particularly advantageous embodiments of the dressing will be described with reference to two illustrations and a number of examples without thereby wishing to unnecessarily restrict the invention.

Figure 2:
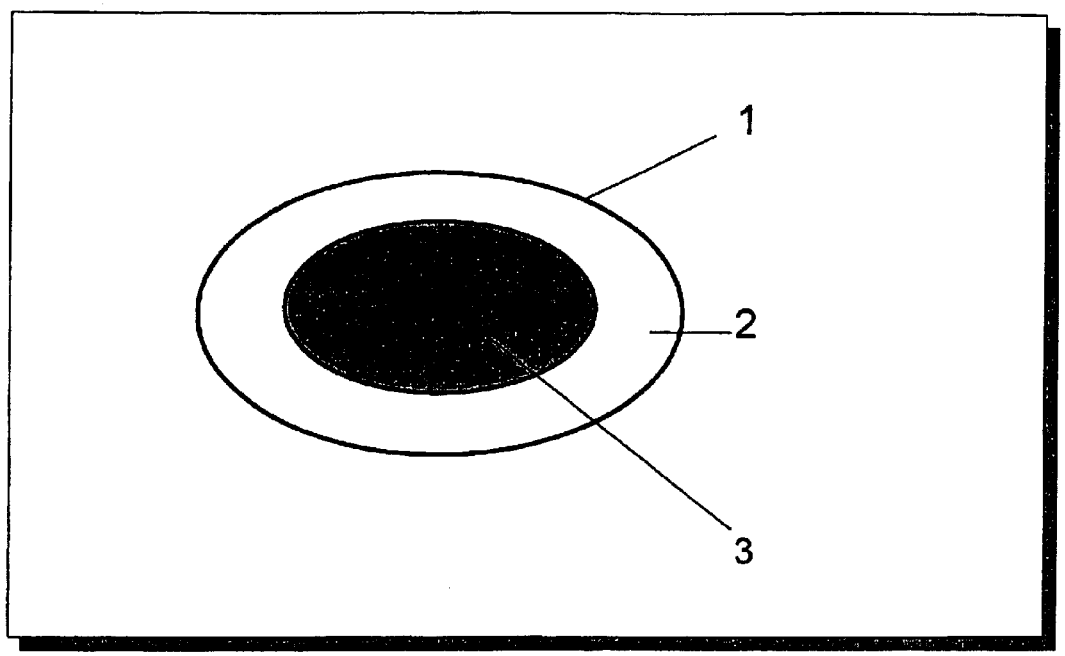

FIG. 1 and FIG. 2 illustrate the preferred geometric shape of the dressing, as used for blister plasters in particular.

The plaster has an ellipsoidal shape and consists of a carrier film 1 which is uniformly coated with an adhesive layer 2.

Centrally located on the adhesive layer 2 is a water vapor pervious polyurethane matrix 3 which is beveled toward the edge of the adhesive layer 2. In the embodiment of the blister plaster shown here, the entire periphery of the adhesive layer 2 is not covered by the polyurethane matrix 3. This results in two concentric zones of chemically different adhesive materials 2, 3 which differ with regard to adherence, absorptivity and cushioning.

The polyurethane matrix 3 is substantially semiconvex and is accordingly comparable to a semiconvex lens.

Finally, the plaster is covered by a siliconized paper 4 to prevent soiling or contamination of the adhesive material 2 or of the matrix 3.

EXAMPLES

Example 1

Dressing Especially for Managing Pressure Points and Blisters a) Carrier Material:

The carrier material of the plaster consists of a multilayered 50 μm thick film of a polyesterurethane (Impranil grade, Bayer AG, Leverkusen).

The layered construction is produced by repeated casting of an approximately 20 g/m² polyesterurethane layer on an approximately 100 μm thick PE film (Waloplast, Wolf Waisrode).

In the course of this process, the composition of the polyesterurethane is gradually altered in such a way that the fraction of soft polyether blocks increases with every coat and hence the hardest coat is the outermost top coat which seals the plaster off from the outside. The PE film is removed from the PU carrier in a later processing step.

TABLE 1

Physical properties of PU carrier material:

| Test | Test method | Unit | Type A 60 g/m² | Type B 80 g/m² |
|---|---|---|---|---|
| Thickness | DIN 53370 | μm | 51 | 70 |
| Basis weight | DIN 53352 | g/m² | 60 | 82 |
| Ultimate tensile strength | DIN EN ISO 527-1/3 | N/cm | 6.6 | 9.6 |
| Elastic deformation | Beiersdorf test method AVS00099* | % | 40.0 | 40.8 |
| Flexural stiffness cd | DIN 53362 | cN*cm² | 0.024 | — |
| Moisture vapor transmission rate | Beiersdorf test method 3VS00008** | g/(m²*24 h) | 770 | 687 |
| Coefficient of friction | DIN 53375 | — | 0.56 | 0.59 |

*Samples 20 mm in width and 100 mm in length are cut from the material at right angles to the machine direction.
The samples are preconditioned at 23 ± 2° C. and 50 ± 5% relative humidity for 24 hours. Each sample is placed in a tensile tester and stretched by 50% and relaxed again (hysteresis) 5 times at a rate of 200 mm/min. The stress-strain curve is recorded, and the result is taken from it after the 5th cycle.
**The test is carried out along the lines of ASTM E 96 (water method) with the following differences:
• The opening of the test vessel is 804 mm²
• The material is preconditioned at 23 ± 2° C. and 50 ± 5% relative humidity for 24 hours
• The distance between the water surface in the test vessel and the sample is 35 ± 5 mm
• The test vessels holding samples are reweighed after 24 hours during which they have been kept in a conditioning cabinet at 37 ± 1.5° C. and 30 ± 3% relative humidity.

b) Outer zone pressure sensitive adhesive coating

The acrylate pressure sensitive adhesive material is knife coated onto a siliconized paper. The uniform coating is then dried in a drying duct at temperatures from 60 to 100° C. The carrier (composite) is laminated on downstream of the drying duct. The composite product is irradiated at 254 nm and 11 to 12 kW for about 1 s to crosslink the adhesive material.

The material used is an acrylate pressure adhesive material of type C having a basis weight of 50 g/m$^2$, consisting of a copolymer of ethylhexyl acrylate, n-butyl acrylate and acrylic acid.

The copolymer has added to it a tackifying resin from the group of the $C_5$ hydrocarbon resins (for example Escorez 5340 from Exxon).

TABLE 2

Physical data of pressure sensitive material on Hostaphan (PET)

| Method | Unit | Acrylate PSA Type C + Escorez 5340 | Comparative Example: Acrylate PSA Type C |
|---|---|---|---|
| Add-on | g/m$^2$ | 50 | 50 |
| Steel/peel force | N/cm | 4.0 | 3.1 |
| Tack (rolling ball)* | cm | 5.3 | 6.5 |

*measured by PSTC-6 (Pressure Sensitive Tape Council test method 6)

TABLE 3

Physical data of PSA coating on PU carrier

| Method | Unit | Type D Combination of carrier-PSA: acrylate PSA Type C + Escorez 5340 on 60 g/m$^2$ carrier (type A) | Type E Combination of carrier-PSA: acrylate PSA Type C + Escorez 5340 on 80 g/m$^2$ carrier (type B) |
|---|---|---|---|
| Add-on | g/m$^2$ | 56 | 56 |
| Steel/(peel force) | N/cm | 6.7 | 7.1 |
| Moisture vapor transmission rate | g/(m$^2$*24 h) | 273 | 254 |

**The test is carried out along the lines of ASTM E 96 (water method) with the following differences:
• The opening of the test vessel is 804 mm$^2$
• The material is preconditioned at 23 ± 2° C. and 50 ± 5% relative humidity for 24 hours
• The distance between the water surface in the test vessel and the sample is 35 ± 5 mm
• The test vessels holding samples are reweighed after 24 hours during which they have been kept in a conditioning cabinet at 37 ± 1.5° C. and 30 ± 3% relative humidity.

c) Inner zone (absorbent zone) pressure sensitive adhesive coating

The coated carrier is placed in a casting mold having a concave, oval depression. The depression is about 1.6 mm deep at the center point of the oval and gradually decreases toward the edges.

The coated carrier is placed in the casting mold with the pressure sensitive adhesive coating face up and 0.7 g of the reactive polyurethane material (Levagel, diisocyanate, catalyst, superabsorbent; index 45 to 55) is applied in the middle of the cavity. The composite is covered with a siliconized PE-coated paper and loaded with a weight until completely cured.

After curing, the PE film is removed and the outer plaster edge is stamped out ovally and concentrically around the central absorbent zone.

TABLE 4

Physical data of plaster in region of absorbent zone

| Test | Method | Unit | Dressing of Ex. 1 based on type D |
|---|---|---|---|
| Liquid absorption | Beiersdorf test method 3VS00004* | g/(g*3 h) | ≧1.0 |
| Moisture vapor transmission rate | Beiersdorf test method 3VS00008** | g/(m$^2$*24 h) | >200 |

*For each plaster a sample having a diameter of 15 mm is punched out from the center and preconditioned at 23 ± 2° C. and 50 ± 5% relative humidity for one hour. The samples are weighed and completely immersed for 3 hours in warm physiological saline solution at 23 ± 0.5° C. The samples are reweighed and the liquid absorption is computed.
**The test is carried out along the lines of ASTM E 96 (water method) with the following differences:
• The opening of the test vessel is 804 mm$^2$
• The material is preconditioned at 23 ± 2° C. and 50 ± 5% relative humidity for 24 hours
• The distance between the water surface in the test vessel and the sample is 35 ± 5 mm
• The test vessels holding samples are reweighed after 24 hours during which they have been kept in a conditioning cabinet at 37 ± 1.5° C. and 30 ± 3% relative humidity.

The result is a self-adhesive wound management product having an outer strongly adhesive zone measuring 43×68 mm and an inner, cushioning and fluid absorbent zone measuring 25×46 mm, which generates a moist wound healing medium. The water vapor pervious polyurethane carrier acts as a barrier against water and bacteria and prevents maceration of the skin underneath the plaster.

Example 2

Dressing Especially for Covering Wounds a) Carrier Material

The carrier material of the plaster is a 35 μm thick film of a polyesterurethane (Impranil grade, Bayer AG, Leverkusen). It is produced by repeated casting of an approximately 20 g/m$^2$ polyesterurethane layer on an approximately 100 μm thick PE film (Waloplast, Wolf Walsrode) which is removed on application of the plaster.

TABLE 5

Physical properties of PU carrier material:

| Test | Method | Unit | Type F 40 g/m² |
|---|---|---|---|
| Thickness | DIN 53370 | μm | 34 |
| Basis weight | DIN 53352 | g/m² | 39 |
| Ultimate tensile strength | DIN EN ISO 527-1/3 | N/cm | >8 |
| Elastic deformation | Beiersdorf test method AVS00099* | % | >42 |
| Moisture vapor transmission rate | Beiersdorf test method 3VS00008** | g/(m²*24 h) | >1300 |

*For each plaster a sample having a diameter of 15 mm is punched out from the center and preconditioned at 23 ± 2° C. and 50 ± 5% relative humidity for one hour. The samples are weighed and completely immersed for 3 hours in warm physiological saline solution at 23 ± 0.5° C. The samples are reweighed and the liquid absorption is computed.
**The test is carried out along the lines of ASTM E 96 (water method) with the following differences:
• The opening of the test vessel is 804 mm²
• The material is preconditioned at 23 ± 2° C. and 50 ± 5% relative humidity for 24 hours
• The distance between the water surface in the test vessel and the sample is 35 ± 5 mm
• The test vessels holding samples are reweighed after 24 hours during which they have been kept in a conditioning cabinet at 37 ± 1.5° C. and 30 ± 3% relative humidity.

b) Outer zone pressure sensitive adhesive coating

The acrylate pressure sensitive adhesive material is knife coated onto a siliconized paper. The uniform coating is then dried in a drying duct at temperatures from 60 to 100° C. The carrier (composite) is laminated on downstream of the drying duct. The composite product is irradiated at 254 nm and 11 to 12 kW for about 1 s to crosslink the adhesive material.

The material used is an acrylate pressure adhesive material of type C having a basis weight of 50 g/m², consisting of a copolymer of ethylhexyl acrylate, n-butyl acrylate and acrylic acid. The physical data of the pressure sensitive adhesive material are discernible from Table 2 under point b) in Example 1.

TABLE 6

Physical data of PSA coating on PU carrier

| | Method | Unit | Type G Combination of carrier-PSA: acrylate PSA Type C on 40 g/m² carrier (type F) |
|---|---|---|---|
| Add-on | | g/m² | 38 |
| Steel/(peel-force) | | N/cm | 3.0 |
| Moisture vapor transmission rate | | g/(m²*24 h) | >300 |

*The test is carried out along the lines of ASTM E 96 (water method) with the following differences:
• The opening of the test vessel is 804 mm²
• The material is preconditioned at 23 ± 2° C. and 50 ± 5% relative humidity for 24 hours
• The distance between the water surface in the test vessel and the sample is 35 ± 5 mm
• The test vessels holding samples are reweighed after 24 hours during which they have been kept in a conditioning cabinet at 37 ± 1.5° C. and 30 ± 3% relative humidity.

c) Inner zone (absorbent zone) pressure sensitive adhesive coating

The coated carrier is placed in a casting mold having a concave, oval depression. The depression is about 1.3 mm deep at the center point of the oval and gradually decreases toward the edges.

The coated carrier is placed in the casting mold with the pressure sensitive adhesive coating face up and 1.6 g of the reactive polyurethane material (Levagel, diisocyanate, catalyst, superabsorbent, titanium dioxide; index 45 to 55) is applied in the middle of the cavity. The composite is covered with a siliconized PE-coated paper and loaded with a weight until completely cured.

After curing, the PE film is provided with a removal aid and the outer plaster edge is stamped outs ovally and concentrically around the central absorbent zone. After the plaster has been adhered to the wound, the PE film is removed from the PV carrier using the removal aid.

TABLE 7

Physical data of plaster in region of absorbent zone

| Test | Method | Unit | Dressing of Ex. 2 based on type G |
|---|---|---|---|
| Liquid absorption | Beiersdorf test method 3VS00004* | g/(g*3 h) | ≧1.0 |
| Moisture vapor transmission rate | Beiersdorf test method 3VS00008** | g/(m²*24 h) | >250 |

*For each plaster a sample having a diameter of 15 mm is punched out from the center and preconditioned at 23 ± 2° C. and 50 ± 5% relative humidity for one hour. The samples are weighed and completely immersed for 3 hours in warm physiological saline solution at 23 ± 0.5° C. The samples are reweighed and the liquid absorption is computed.
**The test is carried out along the lines of ASTM E 96 (water method) with the following differences:
• The opening of the test vessel is 804 mm²
• The material is preconditioned at 23 ± 2° C. and 50 ± 5% relative humidity for 24 hours
• The distance between the water surface in the test vessel and the sample is 35 + 5 mm
• The test vessels holding samples are reweighed after 24 hours during which they have been kept in a conditioning cabinet at 37 ± 1.5° C. and 30 ± 3% relative humidity.

The result is a self-adhesive wound management product having an outer strongly adhesive zone measuring 66×110 mm and an inner, cushioning and fluid absorbent zone measuring 40×80 mm, which generates a moist wound healing medium. The titanium dioxide makes the absorption zone appear milky and so the absorption zone covers the wound not only physically but also visually.

The water vapor pervious polyurethane carrier acts as a barrier against water and bacteria and prevents maceration of the skin underneath the plaster.

What is claimed is:

1. A dressing suitable for covering wounds or for preventing or treating blisters, said dressing comprising:

a) a transparent multilayered water vapor pervious carrier film comprising polyurethane;

b) an adhesive layer uniformly disposed on said water vapor pervious carrier film; and c) a water vapor pervious polyurethane matrix centrally disposed on the adhesive layer, wherein the water vapor pervious polyurethane matrix is beveled from a central point thereof to an edge thereof adjoining the adhesive layer, and wherein the vapor water pervious polyurethane matrix does not fully cover the adhesive layer.

2. The dressing of claim 1, wherein the transparent multilayered water vapor pervious carrier film is between 60 to 80 μm in thickness.

3. The dressing of claim 1, wherein the adhesive layer comprises polyacrylate.

4. The dressing of claim 1, wherein the adhesive layer is between 35 to 50 µm in thickness.

5. The dressing of claim 1, which further comprises a covering over its entire width, said covering being an adhesive rejecting carrier material.

6. The dressing of claim 5, wherein the adhesive rejecting carrier material comprises siliconized paper.

7. A method of covering a wound comprising applying the dressing according to claim 1 to skin containing the wound.

8. A method of preventing or treating a blister comprising applying to skin susceptible to developing a blister or to skin containing a blister the dressing according to claim 1.

9. The dressing of claim 1, wherein the transparent multilayered water vapor pervious carrier film comprises an upper layer of a hard polyurethane coating.

* * * * *